United States Patent
Chiodo (10) Patent No.: US 7,865,226 B2
(45) Date of Patent: Jan. 4, 2011

(54) SPECIMEN POSITIONING SYSTEM FOR IMAGING MACHINES

(76) Inventor: Chris D. Chiodo, 29277 Newport, Warren, MI (US) 48093

( * ) Notice: Subject to any disclaimer, the term of this patent is extended or adjusted under 35 U.S.C. 154(b) by 723 days.

(21) Appl. No.: 11/346,850

(22) Filed: Feb. 3, 2006

(65) Prior Publication Data

US 2007/0238946 A1    Oct. 11, 2007

(51) Int. Cl.
*A61B 5/05* (2006.01)
*A01K 15/04* (2006.01)

(52) U.S. Cl. ........................ 600/407; 119/751

(58) Field of Classification Search ........ 600/407, 600/410–411, 415, 417, 422; 606/130; 324/318–322; 378/63, 65, 200; 119/720–724, 751–757

See application file for complete search history.

(56) References Cited

U.S. PATENT DOCUMENTS

| | | | | |
|---|---|---|---|---|
| 2,773,477 | A * | 12/1956 | Michael | 119/756 |
| 4,269,149 | A * | 5/1981 | Thomas | 119/729 |
| 4,534,050 | A * | 8/1985 | Smith | 378/81 |
| 5,281,232 | A * | 1/1994 | Hamilton et al. | 606/130 |
| 5,311,868 | A * | 5/1994 | Carbini et al. | 600/417 |
| 5,324,911 | A * | 6/1994 | Cranston et al. | 219/218 |
| 5,391,877 | A * | 2/1995 | Marks | 250/363.04 |
| 5,681,326 | A * | 10/1997 | Lax | 606/130 |
| 5,797,924 | A * | 8/1998 | Schulte et al. | 606/130 |
| 6,138,302 | A * | 10/2000 | Sashin et al. | 5/600 |
| 6,205,347 | B1 * | 3/2001 | Morgan et al. | 600/407 |
| 6,258,103 | B1 * | 7/2001 | Saracione | 606/130 |
| 6,275,723 | B1 * | 8/2001 | Ferris et al. | 600/417 |
| 6,591,127 | B1 * | 7/2003 | McKinnon | 600/411 |
| 6,615,063 | B1 * | 9/2003 | Ntziachristos et al. | 600/312 |
| 6,711,430 | B1 * | 3/2004 | Ferris et al. | 600/417 |
| 6,754,519 | B1 * | 6/2004 | Hefetz et al. | 600/407 |
| 6,754,520 | B2 * | 6/2004 | DeSilets et al. | 600/415 |
| 6,869,593 | B2 * | 3/2005 | Frangioni | 424/9.6 |
| 6,873,156 | B2 * | 3/2005 | Ferris et al. | 324/318 |
| 6,925,319 | B2 * | 8/2005 | McKinnon | 600/407 |
| 6,941,164 | B2 * | 9/2005 | Hajaj et al. | 600/407 |
| 6,961,606 | B2 * | 11/2005 | DeSilets et al. | 600/415 |
| 7,135,978 | B2 * | 11/2006 | Gisselberg et al. | 340/572.5 |
| 7,146,936 | B2 * | 12/2006 | Dazai et al. | 119/756 |
| 7,190,991 | B2 * | 3/2007 | Cable et al. | 600/407 |
| 7,289,839 | B2 * | 10/2007 | Dimmer et al. | 600/407 |
| 7,383,076 | B2 * | 6/2008 | Ntziachristos et al. | 600/473 |
| 7,403,812 | B2 * | 7/2008 | Rice et al. | 600/473 |
| 7,412,027 | B2 * | 8/2008 | Yakubovsky et al. | 378/63 |
| 7,414,403 | B2 * | 8/2008 | Chiodo | 324/321 |
| 2003/0069471 | A1 * | 4/2003 | Nakanishi et al. | 600/101 |
| 2003/0078489 | A1 * | 4/2003 | DeSilets et al. | 600/407 |
| 2003/0086535 | A1 * | 5/2003 | Teppaz et al. | 378/207 |
| 2003/0181808 | A1 * | 9/2003 | McKinnon | 600/411 |
| 2003/0229312 | A1 * | 12/2003 | Smith et al. | 604/152 |
| 2004/0028611 | A1 * | 2/2004 | Frangioni | 424/9.6 |
| 2004/0066909 | A1 * | 4/2004 | Lonn et al. | 378/901 |

(Continued)

*Primary Examiner*—Long V Le
*Assistant Examiner*—Angela M Hoffa
(74) *Attorney, Agent, or Firm*—Lawrence J. Shurupoff (57) ABSTRACT

An animal holder is provided with a specialized coupling that is releasably mountable to a number of different imaging machines such as X-ray, CAT, MRI and PET machines. Composite images created from combining images from such different machines are particularly clear due to the predetermined alignment of the animal holder within the center of the field of view of each machine.

9 Claims, 5 Drawing Sheets

U.S. PATENT DOCUMENTS

| | | | |
|---|---|---|---|
| 2004/0210126 A1* | 10/2004 | Hajaj et al. | 600/407 |
| 2005/0027190 A1* | 2/2005 | Chiodo | 600/415 |
| 2005/0056234 A1* | 3/2005 | Dazai et al. | 119/757 |
| 2005/0215878 A1* | 9/2005 | Zan | 600/407 |
| 2006/0064000 A1* | 3/2006 | Vizard et al. | 600/407 |
| 2006/0078501 A1* | 4/2006 | Goertz et al. | 424/9.52 |
| 2008/0212859 A1* | 9/2008 | Da Silva et al. | 382/131 |
| 2009/0000567 A1* | 1/2009 | Hadjioannou et al. | 119/755 |

* cited by examiner

SPECIMEN POSITIONING SYSTEM FOR IMAGING MACHINES

GOVERNMENT RIGHTS

This invention was made with government support under contracts 1 R41 NS050141-01 and 3 R41 NS050141-0151 awarded by The National Institutes of Health (NIH). The government has certain rights in the invention.

BACKGROUND OF THE INVENTION

1. Field of the Invention

The present invention relates in general to apparatus for holding a specimen, such as a laboratory animal, in a fixed position during an imaging procedure such as X-ray, CAT and CT scans, MRI and PET imaging. The invention relates in particular to such apparatus which provide for the accurate repeatable positioning of a specimen time and again within the same imaging machine or within a number of different imaging machines.

2. Description of Prior Developments

In the field of medical research and patient treatment, it is often desirable to take a series of pictures or images of an anatomical feature, such as the brain, heart, knee or other organ or musculoskeletal feature over a period of time. Doctors and researchers need to review and study such features over time to understand the development, aging and changes normally associated with such features. Doctors and researchers also need to study such features as a function of the duration of a disease or pathological condition such as cancers and tumors. Doctors and researchers also need to review and monitor physiological changes in anatomical features as a function of time due to various treatments such as pharmacological and surgical treatments.

Different imaging machines are best suited for imaging different types of anatomical features. For example, bone is generally better imaged by X-ray machines and computerized axial tomography (CAT or CT) scanning machines, while soft tissue is generally better imaged by magnetic resonance imaging (MRI) machines. Imaging techniques such as bioluminescent, fluorescent and photon emission tomography (PET) generally provide better bio-functional data while MRI and CT imaging generally provide better structural and anatomical data.

As a result of the strengths and weaknesses of the various imaging techniques, researchers have come to rely on the use of a combination of images from different imaging machines to produce compound or superimposed images which integrate the best features from each imaging technique. This multiple image technique requires a specimen to be imaged on and moved between a series of different imaging machines.

In order to produce accurate and clear composite images, the specimen must be accurately and repeatably positioned within each imaging machine to allow for the accurate coregistration of the various images. This has proved to be a difficult, labor intensive and time consuming setup, adjustment and alignment process.

SUMMARY OF THE INVENTION

The present invention has been developed to assist doctors and researchers in accurately and repeatably imaging the same specimen, such as a laboratory mouse or rat, over an extended period of time, such as in longitudinal time course studies, using one or more imaging machines. In accordance with the invention, a specimen may be transported in-situ from one imaging machine to the next in such a predetermined position as to facilitate the coregistration of images from one or more of the imaging machines.

That is, the present invention minimizes the variability of animal or specimen placement within the field of view of any one or more of a series of different imaging machines. This is achieved by enabling the removal of the animal or specimen from one imaging machine and the subsequent placement of the animal or specimen in the same or different imaging machine in exactly the same relative position and location time after time. This is particularly advantageous for longitudinal time course studies, where the specimen is imaged at one point in time, removed from the imaging machine and at a later time placed back into the same machine in exactly the same position and imaged again.

The present invention also minimizes the variability of animal or specimen placement when the same animal or specimen is taken from one imaging machine to the next. Images from each of a series of imaging machines may be taken of the same animal or specimen in the same position as the image taken in the first imaging machine. An animal or specimen is loaded and locked into position in accordance with the invention, and moved to each imaging device within a single common holder.

This process, apparatus and technique not only eliminates multiple setups in multiple machines, it also eliminates multiple handlings of the animal or specimen. This is particularly advantageous in those cases where the animal or specimen is contagious. Moreover, this process, apparatus and technique improves specimen position repeatability and machine setup time and throughput.

As noted above, researchers typically superimpose images from different imaging machines to form a single coregistered or composite image, taking the best features from MRI, X-ray, PET and other machines to maximize the clarity and information provided within the images. The present invention provides for the creation of clear compound images from different imaging machines by accurately positioning a specimen or patient in the same relative position in each machine. This increases the quality and reliability of coregistration of the individual images. It also increases the speed and accuracy of specialized software used to create the compound images from the different images produced by the different machines.

The present invention provides two main sections or assemblies for accomplishing the accurate and repeatable positioning of laboratory specimens such as rats and mice within the "sweet spot" or field of view of each one of various imaging machines. The first main section is a spacing or positioning receiver section and the second section is a specimen or animal holding section. A specialized coupling is provided to accurately align and connect the specimen or animal holding system to the positioning receiver assembly which can be permanently or removably mounted to an imaging machine.

In accordance with the invention, the animal holding system is releasably coupled to the positioning receiver assembly. The animal holding system is mountable interchangeably on a positioning receiver assembly on one or more imaging machines. The positioning receiver assemblies are specially adapted to mount on each respective imaging machine in such a manner that when the animal holding system is coupled to the positioning receiver assembly, the animal holding system optimally positions the animal within the field of view on each respective imaging machine.

The specialized coupling between the animal holding assembly and the positioning receiver assembly includes a male component and a female component. Each positioning receiver assembly includes the female component portion of the coupling along with a control lever to engage, lock and release the animal holding system. The animal holding system includes a male component portion of the coupling. When the male coupling portion is inserted into the female receiver coupling portion and engaged and locked, a precision, reproducible alignment coupling and connection is formed.

The combination of the positioning receiver assembly and the animal holding system produces an animal management system. From time to time an additional assembly called a positioning assembly system may be required to facilitate the placement of the animal management system into an imaging machine. This is typically required on MRI machines due to their inherent design. Each positioning assembly system, and/ or as the case may be, positioning receiver assembly can be kept mounted to its respective imaging machine so that the animal holding system can be coupled to the imaging machine directly via the positioning receiver assembly or indirectly via the positioning assembly system for an MRI machine, in a highly repeatable way.

The aforementioned objects features and advantages of the invention will in part, be pointed out with particularity, and will, in part, become obvious from the following more detailed description of the invention, taken in conjunction with the accompanying drawings, which form an integral part thereof.

DETAILED DESCRIPTION OF THE PREFERRED EMBODIMENTS

The present invention will now be described in conjunction with the drawings, beginning with FIG. 1 which shows an animal management system or specimen positioning system 10 constructed in accordance with a first embodiment of the invention. The positioning system 10 is adapted for use in an MRI positioning assembly such as disclosed in US patent application publication number US 2005/0027190A1, filed Aug. 10, 2001, under application Ser. No. 10/631,226, and which is incorporated herein in its entirety by reference.

While the specimen positioning assembly in US 2005/ 0027190 provides for a unitary specimen positioning assembly, the present invention provides for an equivalent modular multicomponent positioning system. That is, the positioning system 10 of the present invention includes a detachable modular specimen holder or animal holding system 12 which is removably and selectively mountable on a positioning receiver assembly 14 which is adapted for mounting on an imaging machine.

A modular coupling 16 is provided between the animal holding system 12 and the positioning receiver assembly 14 for accurately and repeatably coupling the animal holding system 12 to the positioning receiver assembly 14 to form a positioning system 10. Coupling 16 includes a male coupling portion 18 mounted on an outer end of the animal holding system 12 and a female coupling portion 20 mounted on an inner end of the positioning receiver assembly 14. If desired, the male and female portions 18, 20 of coupling 16 can be reversed, as long as all other compatible systems 10 are similarly adapted.

Once the male coupling portion 18 is inserted within the female coupling portion 20, a male keying member 22 projecting from a predetermine circumferential or clockwise position (such as 12 o'clock) on the male coupling portion 18 is inserted and guided into a complementary keying slot 24 formed in a predetermined circumferential or clockwise position (such as 12 o'clock) on the female coupling portion 20 so as to circumferentially align the animal holding system 12 with the positioning receiver assembly 14. This clockwise alignment ensures proper, accurate and repeatable placement of a specimen held within the animal holding system 12 within a known, generally horizontal, axial plane within the field of view of an imaging machine, as discussed further below.

Once the male coupling portion 18 is fully inserted within the female coupling portion 20, a cam ring 26 with internal circumferentially-extending cam ramps mounted within the female coupling portion 20 can be rotated by a cam lever or cam grip tab 28 to radially compress a circumferentially-spaced series of balls 29 loosely held within coupling portion 20 and thereby axially wedge and lock the male coupling portion 18 into a tight axial abutment against a radial registration surface on the female coupling portion 20. At the same time, a frustoconical male plug portion 30 on the male coupling member 18 is tightly seated and centered within a complimentary frustoconical female socket portion 32 formed within the female coupling portion 20.

This conical nesting centers the male coupling portion 18 within the female coupling portion 20 and thereby coaxially aligns the animal holding system 12 with the positioning receiver assembly 14. At the same time, the tight axial abutment between the male and female coupling portions 18, 20 accurately axially locates and registers the animal holding system 12 with respect to the positioning receiver assembly 14.

In order to release and separate the male coupling portion 18 from the female coupling portion 20, an operator need only rotate or push the cam tab 28 in an opposite direction to that of the locking direction. The animal holding system 12 can then be easily removed and placed in another positioning receiver assembly 14 in a different type of imaging machine. Additional details of the quick-connect and quick disconnect coupling 16 are provided in U.S. patent application Ser. No. 11/346,851, filed Feb. 3, 2006, titled, Coupling Assembly for Animal Management Systems.

Figure 1:
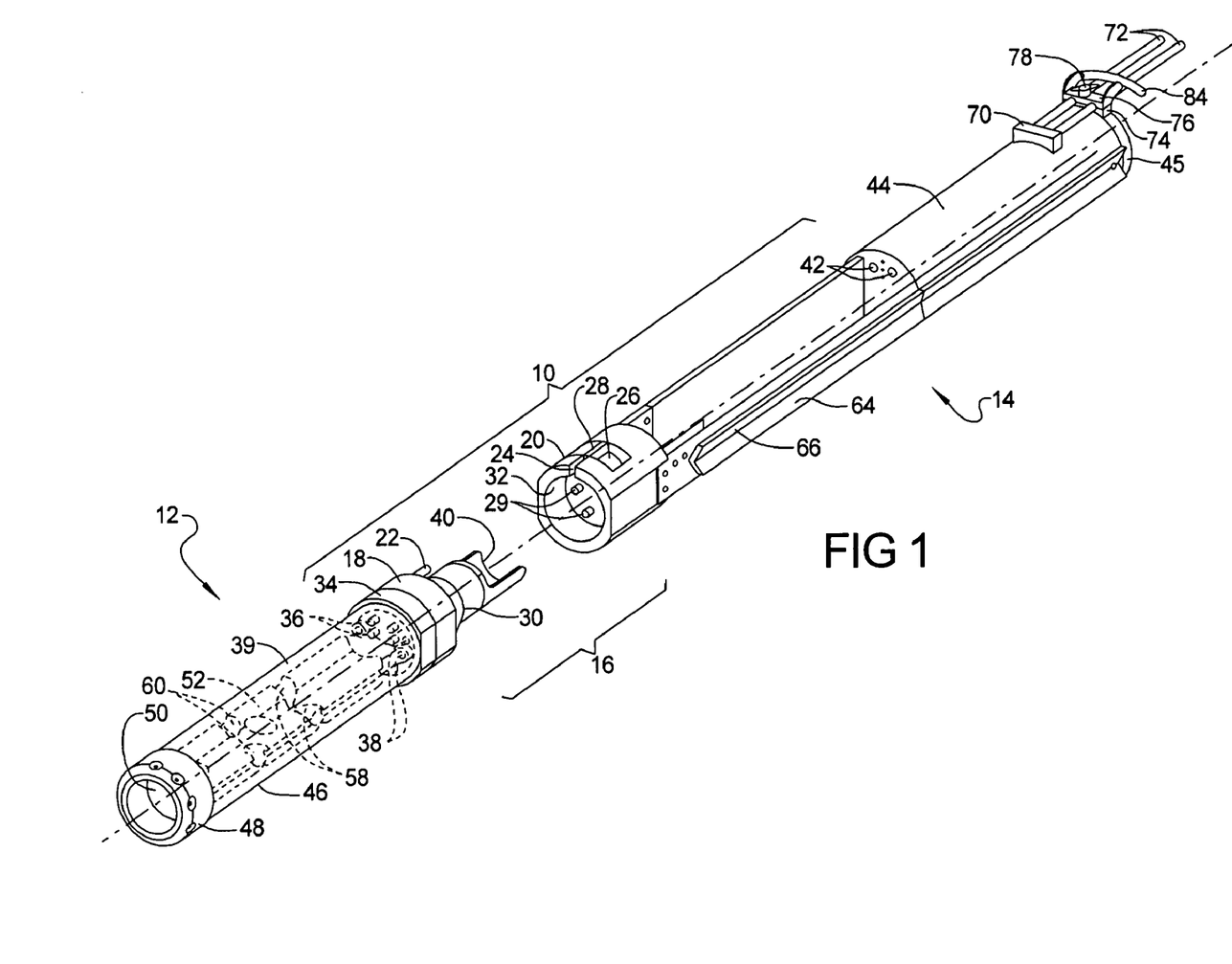
FIG. 1 is a perspective exploded view of a first embodiment of an animal management system, also called a specimen positioning system, constructed in accordance with a first embodiment of the invention and adapted for use in an MRI machine.

As further shown in FIG. 1, the animal holding system 12 further includes an interconnection panel 34 which includes various ports 36 for the passage of fluids such as anesthesia gasses, and various electrical connectors 38 for the connection of sensor lead wires from ECG sensors and respiratory sensors, for example, located within animal holding chamber 39. The fluid ports 36 and electrical connectors 38 communicate with aligned passages formed through the male coupling portion 18 to which the panel 34 is connected.

A lead support tray or trough 40 receives and supports the electrical wires and fluid tubes exiting the outer end of the male coupling portion 18. These wires and tubes extend from within the panel 34, through channels or passages through the male coupling portion 18 and outwardly along the positioning receiver assembly 14. They then pass through conduits 42 formed through the cylindrical base 44 of the positioning receiver assembly 14. The tubes and electrical leads can then be respectively connected to external sources of fluids and to remote monitoring devices via an outer connector plate 45.

The specimen or animal chamber 39 includes a cylindrical tube 46 connected and hermetically sealed to the interconnection panel 34. Tube 46 may be made of clear or transparent plastic or glass. The inner end of tube 46 may terminate in a semihemispherical bulb in a manner similar to a common test tube. Alternatively, an end cap 48 can be threaded onto an inner threaded open end of tube 46 as shown in FIG. 1. In this case, a porous filter 50 is clamped or mounted to the inner end of tube 46 by end cap 48.

In order to accurately position and restrain a specimen, such as a laboratory rat, within the animal holding system 12, a live specimen alignment bed 52 is accurately positioned axially and circumferentially (clockwise) within tube 39. The outer end of the alignment bed 52 is accurately and removably mounted to the interconnection panel 34 by a pair of eyelets 54 (FIG. 3) which aligns with threaded bores in the interconnection panel 34. Threaded fasteners such as plastic screws can be used to fix the alignment bed 52 to the interconnection panel 34 via eyelets 54.

The alignment bed 52 is formed as a unitary integral support surface with a central longitudinal groove or channel 56 for accurately aligning and holding the body of an animal centrally within the tube 39. Channel 56 extends closely parallel with the central axis 57 of tube 39. Grooves or slots 58 are formed in alignment bed 52 for positioning and fixing in predetermined place the rear legs of an animal. Grooves or slots 60 are formed in alignment bed 52 for positioning and fixing in predetermined place the front legs of an animal.

A bite bar 62 is placed at the inner end of the alignment bed 52 to anchor an animal's teeth in a known axial position which corresponds to a position closely adjacent to the centerline of the field of view of each imaging machine into which the positioning system 10 is subsequently mounted. Ear bars and/or a head clamp (not shown) may also be provided to lock an animal's head in a predetermined axial location and radial orientation on the alignment bed 52.

The positioning receiver assembly 14 in FIG. 1 is specially configured to operate within a commercially available MRI machine. In this case, the positioning receiver assembly 14 is provided with a pair of diametrically-opposed axially-extending side rails 64. Each side rail 64 has a V-shaped axial groove 66 which self-aligns within a positioning assembly by sliding over a pair of complementary cylindrical rods in the manner described in US patent application publication number US 2005/0027190 A1, mentioned above.

While the specimen positioning assembly of US 2005/0027190 A1 relies on a fixed exterior annular end plate to abut against a mounting plate on a positioning assembly on the exterior of an MRI machine to provide proper registration and alignment of the specimen positioning assembly within the MRI machine, the specimen positioning system 10 of FIG. 1 has an axially-adjustable stop pad 70 which allows for axial adjustment of the positioning system 10 within the bore of an MRI machine.

Stop pad 70 is connected to a pair of slide rods 72 that are frictionally clamped between a lower double V-block 74 and an upper clamp bar 76. A thumb screw 78 is turned to raise and lower the clamp bar 76 to adjust the clamping force on the slide rods 72 so as to set the axial position of the stop pad 70, as desired. This allows a researcher to axially adjust and align a desired portion of an animal within the field of view of an imaging machine. A standard position for alignment of the brain of the specimen can be set at the fully extended (inward) position of the stop pad 80.

The lower double V-block 74 is fixed to the outer connector plate 45 through which fluid and electrical leads can pass, as described above. An arch-shaped carrying handle 84 is connected to the outer connector plate 45 to allow an operator to carry the entire positioning system 10 as a unit, as desired, such as from one imaging machine to the next.

Figure 2:
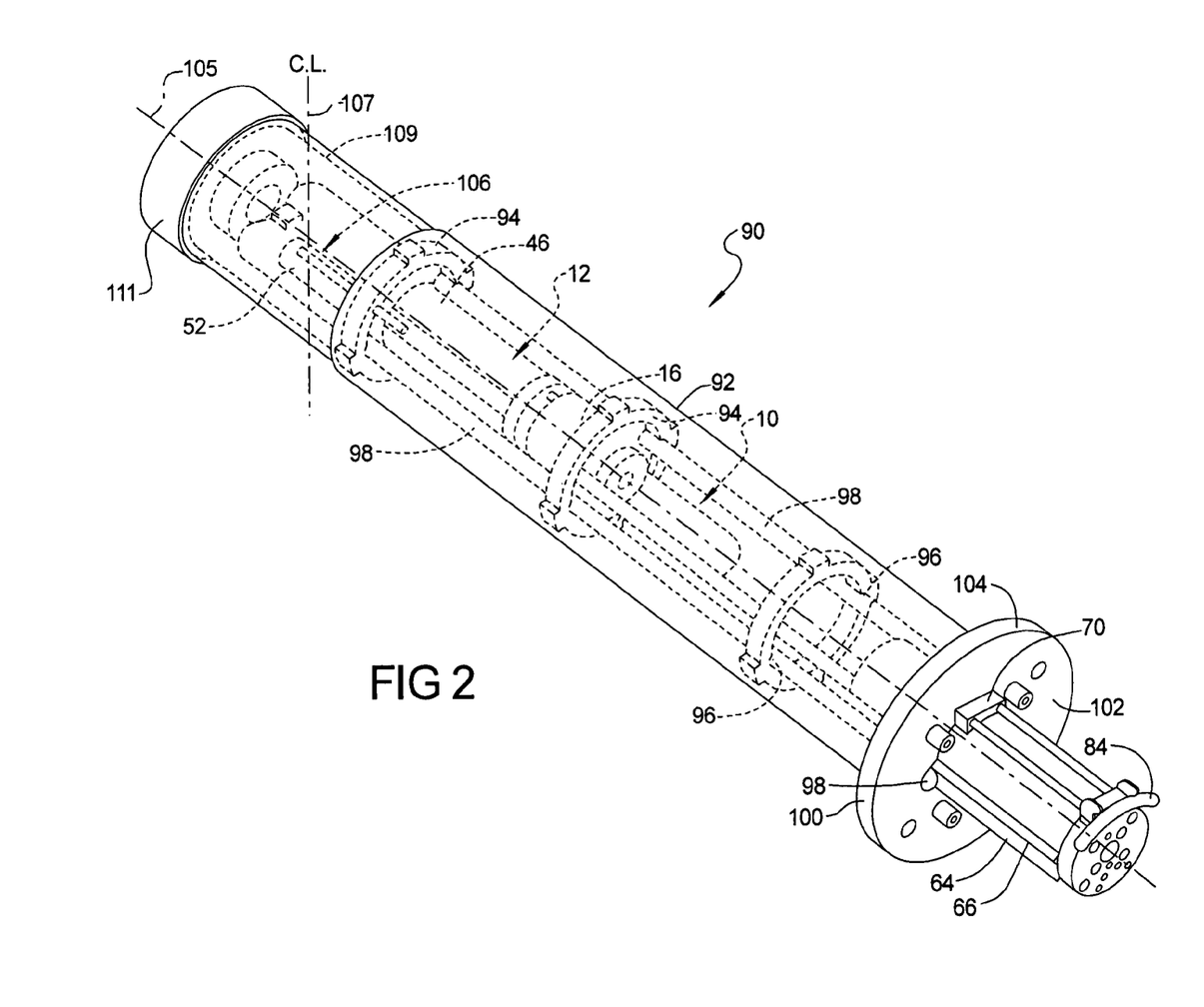
FIG. 2 is a perspective view of the animal management system of FIG. 1 mounted in a positioning assembly system adapted for mounting within the bore of an MRI machine.

The positioning system 10 of FIG. 1 is shown mounted within a mating positioning assembly system 90 in FIG. 2. The positioning assembly system 90 of FIG. 2 is adapted to be mounted within the bore of an MRI machine of conventional construction in a manner similar to that described in US 2005/0027190 A1, noted above.

The positioning assembly system 90 of FIG. 2 includes an elongated cylindrical tube 92 having a diameter closely matching that of the bore of an MRI machine within which the positioning assembly system is to be mounted. A series of axially-spaced mounting rings 94 is mounted within the tube 92 with plastic fasteners or adhesives. Each mounting ring 94 is formed with a pair of diametrically-opposed V-shaped notches 96 for accurately centering and mounting a pair of diametrically-opposed axially-aligned cylindrical guide rods 98.

Guide rods 98 are fixed to each of the mounting rings 94 and to a front mounting plate 100 with plastic fasteners, such as plastic screws. Adhesives can also be used for this purpose. The cylindrical tube 92 is also attached to the front mounting plate 100 with adhesives or plastic brackets or retainers.

As further seen in FIG. 2, the positioning system 10 of FIG. 1 is inserted into the positioning assembly system 90 by sliding the V-grooves 66 on side rails 64 over the diametrically-opposed cylindrical guide rods 98 until the stop pad 70 abuts the outer face 102 of the front mounting plate 100. In actual practice, the tube 92 of the positioning assembly system 90 will be premounted within the bore of an MRI machine, similar to a shell in a cannon bore, and the inner face 104 of the front mounting plate 100 will be tightly fixed against an exterior alignment and registration surface of the MRI machine.

The front mounting plate 100 will be fixed to the alignment and registration surface of the MRI machine in a predetermined clockwise orientation, such that the cylindrical guide rods 98 are aligned within a horizontal plane passing through the central axis 105 of the tube 92 and through the coaxially aligned bore of the MRI machine. This relationship ensures that the side rails 64 on the positioning receiver assembly 14 will be similarly aligned along with any animal holding system 12 mounted on the positioning receiver assembly 14.

The axial distance between the front face of the fully inwardly extended stop pad 70 and a predetermined imaging area 106 on the specimen alignment bed 52 is accurately dimensioned so that when the positioning system 10 is fully inserted within the positioning assembly system 90, the imaging area 106 is centrally aligned within and around the centerline or center of the field of view 107 of the imaging machine, as well as along axis 105. In this embodiment, positioning system 10 and positioning system 90 abut and register with one another to center and position the brain of a laboratory rat at the intersection of central axis 105 and centerline 107 of the imaging machine for optimal imaging of the brain.

As further seen in phantom in FIG. 2, a cylindrical tubular radio frequency coil or RF probe 109 is set a predetermined axial length from the mounting plate 100. In this manner, when the positioning system 10 is inserted within the positioning system 90, the axial location of the animal holding system 12, which is also axially set and referenced off mounting plate 100, is optimally positioned axially and coaxially within the RF probe 109. Probe can be fixed to end wall 111 with plastic screws.

Once a specimen is imaged within an imaging machine fitted with the positioning assembly system 90 of FIG. 2, the positioning system 10 is withdrawn from the positioning assembly 90 and from the imaging machine by a simple axial pull on handle 84.

The positioning system 10 simply slides in and out of the positioning assembly 90, which may be permanently, semi-permanently or removably mounted to the imaging machine. Once the positioning system 10 is removed, the animal holding system 12 can be accessed and quickly released from the positioning receiver assembly 14. This is done by unlocking and releasing the coupling 16 and axially sliding the male coupling portion 18 out of the female coupling portion 20.

Figure 3:
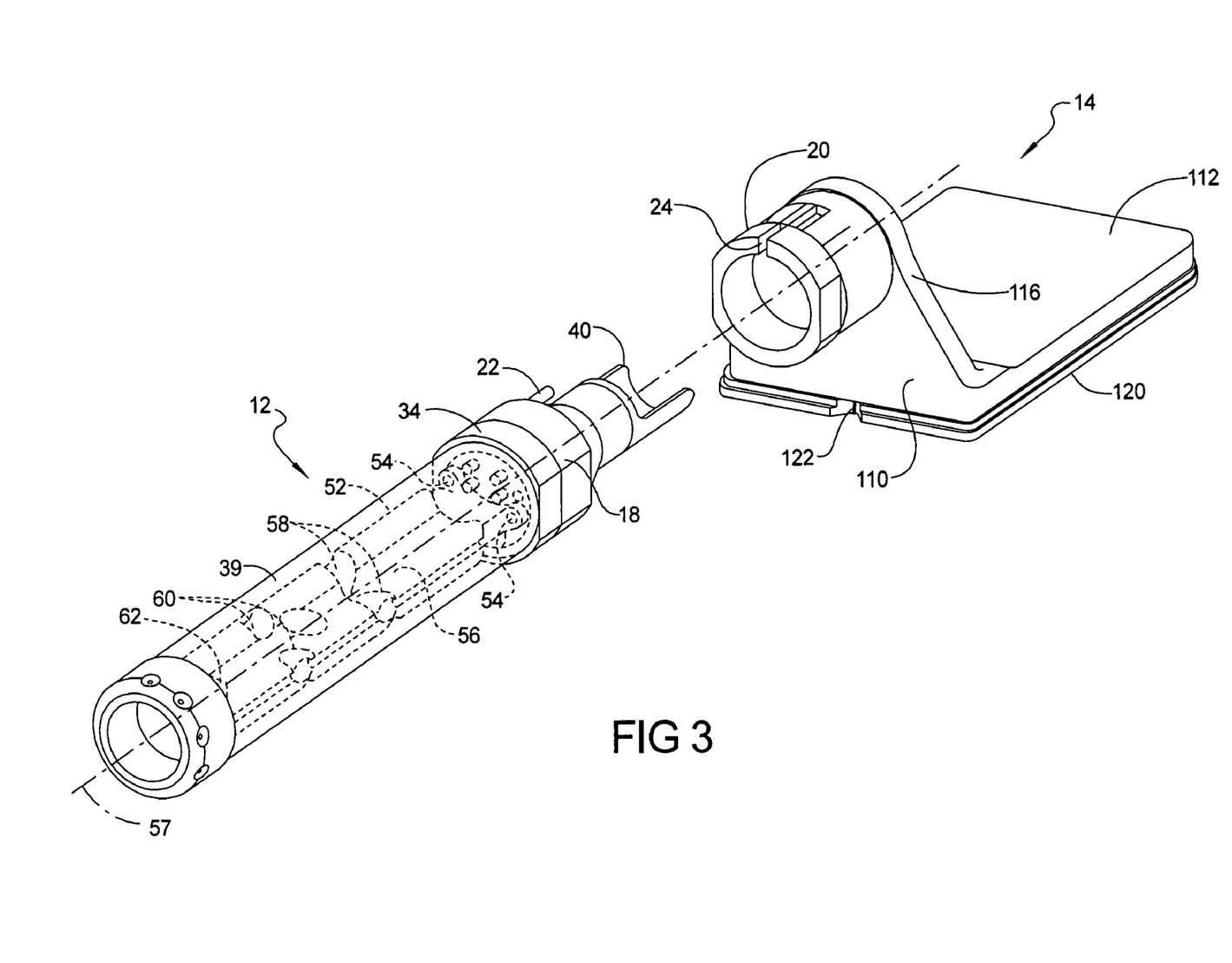
FIG. 3 is a perspective exploded view of a second embodiment of the invention showing an animal management system adapted for use in a CT or PET imaging machine.
Figure 4:
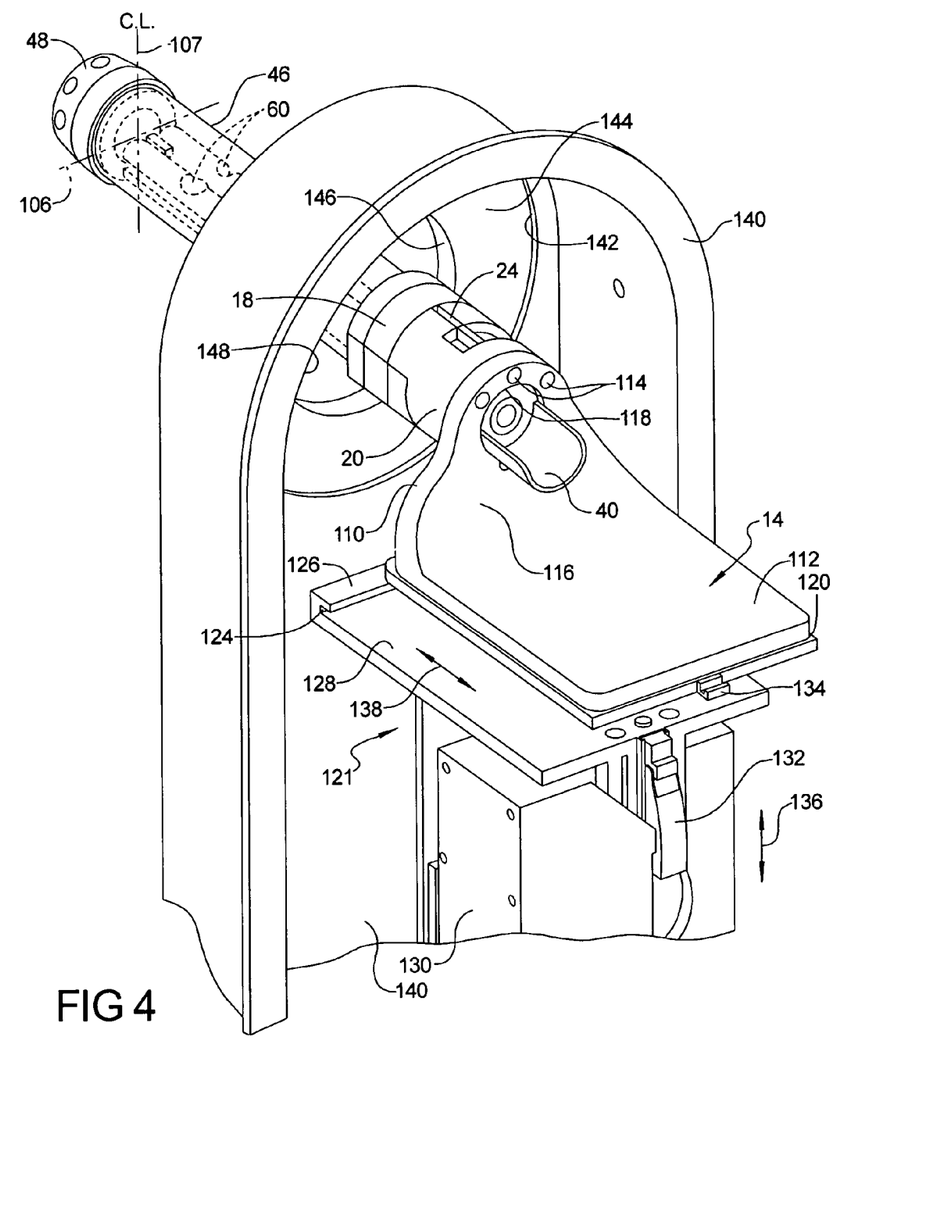
FIG. 4 is a partial perspective view of the animal management system of FIG. 3 mounted to a bracket adapted to be removably clamped or mounted on the outer face of a CT imaging machine and inserted within the bore of a CT imaging machine.
Figure 5:
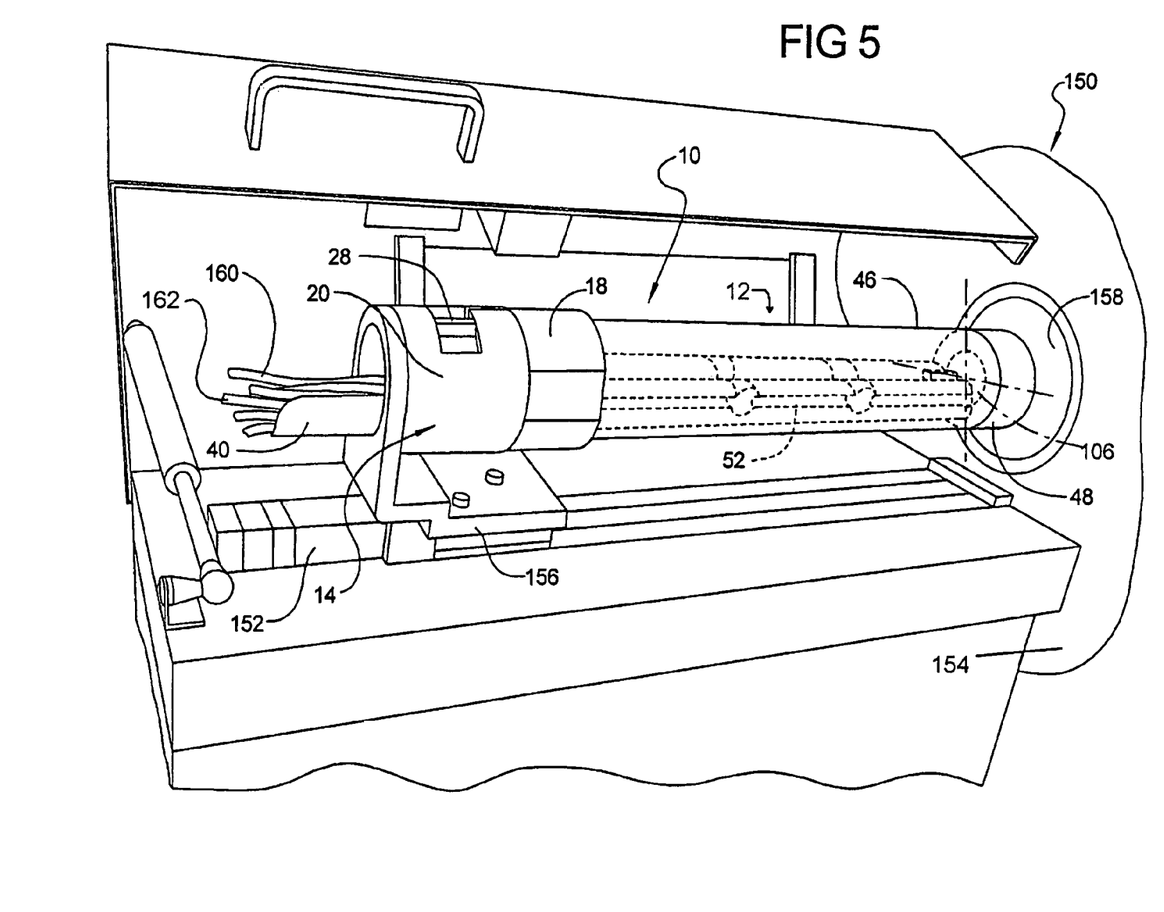
FIG. 5 is a perspective view of a third embodiment of the invention showing the animal management system mounted to another CT machine.

At this point, animal holding system 12 with a specimen still fixed within chamber 39 can be mounted to another positioning receiver assembly 14, such as shown in FIGS. 3, 4 and 5. In FIGS. 3 and 4, the positioning receiver assembly 14 is adapted for mounting to a micro CT and/or to a micro PET imaging machine of conventional design.

The positioning receiver assembly 14 of FIGS. 3 and 4 is in the form of a relatively simple bracket and plate configuration. A modular female coupling portion 20 is accurately and rigidly mounted in a predetermined axial and circumferential orientation to the front face of a vertical mounting bracket 110 fixed to a flat rectangular horizontal mounting plate 112.

As in the previous example, the circumferential or clockwise orientation of the female coupling portion 20 is closely and accurately fixed so that when the male keying member 22 on the male coupling portion 18 on the animal holding system 12 is inserted in the keying slot 24 in the female coupling portion 20, the animal holding system 12 will be fixed in a corresponding predetermined clockwise position with respect to the positioning receiver assembly 14. As seen in FIG. 4, the female coupling portion 20 is rigidly fixed to the mounting bracket 110 by a set of mounting screws 114.

Bracket 110 may include a mounting arch or collar 116 which surrounds a circular bore 118 (FIG. 4) formed through the upper portion of bracket 110. A lead support tray 40 extends through bore 118 for the support of fluid tubing and electrical sensor wires. In the example shown, bracket 110 is arranged substantially perpendicular to the mounting plate 112.

A mounting flange 120 is fixed to the bottom of mounting plate 112 for aligning and mounting the positioning receiver assembly 14 to an external support assembly 121 for a CT or PET machine, as shown in FIG. 4. A V-shaped notch 122 (FIG. 3) is formed in the center of the inner edge of mounting flange 120.

As seen in FIG. 4, an end block 126 is fixed to a mounting pad 128 on an actuator assembly 130 adapted for mounting on the outer surface of a CT imaging machine. The positioning receiver assembly 14, with the animal holder system 12 attached, is placed on the mounting pad 128 and pushed forwardly against end block 126. A V-shaped key (not shown) projecting outwardly from the center of end block 126 keys into the V-shaped notch 122 on mounting flange 120 and properly centers the positioning receiver assembly 14 on mounting pad 128.

At the same time, the front edge of mounting flange 120 is fully seated within a channel 124 in end block 126 to further align and position the positioning receiver assembly 14 on mounting pad 128. A clasp or over-center snap-fit type connector or latch 132 then latches over a tab or tang 134 extending outwardly from the outer edge of the mounting flange 120 to anchor and lock the positioning receiver assembly in a predetermined position. In FIG. 4, the positioning receiver assembly 14 is shown positioned just above the mounting pad 128, just prior to being anchored in position by clasp 132 and tang 134.

The actuator assembly 130 is adapted to drive the mounting pad 128 and attached positioning receiver assembly 14 up and down as shown by arrows 136 and in and out of a magnet bore as shown by arrows 138. The actuator assembly 130 can be controlled by a microcontroller or other digital indexing controller.

As further seen in FIG. 4, the actuator assembly 130 is mounted in a known predetermined orientation and position to an elongated pan-shaped bracket 140 having a large circular aperture 142 formed in its upper end portion. Bracket 140 is fixed to the front face 144 of a CT machine, such that the circular aperture 142 concentrically surrounds the circular entrance 146 to the machine bore 148 of the CT machine (not shown).

Since the dimensions and spatial locations of the machine bore 148, bracket 140, actuator assembly 130, mounting pad 128, positioning receiver assembly 14 and animal holding system 12 are mutually coordinated and predetermined, the imaging area 106 within the animal holding system 12 is preset and predetermined to coincide with the "sweet spot" or centerline 107 of the imaging machine, as in the previous example.

FIG. 5 shows yet another embodiment of the invention, wherein the specimen positioning system 10 is mounted on yet another different imaging machine, in this case a CT scanner 150. The system 10 is supported on a linear drive table 152 connected to the front surface 154 of a CT machine.

A stepped L-shaped bracket assembly 156 fixed to and supporting the positioning receiver assembly 14 mounts the animal holding system 12 to the drive table 152 for controlled linear movement into and out of the bore 158 of the imaging machine. In this example, electrical leads 160 and fluid tubing 162 are shown exiting the lead support tray 40 extending from the female coupling portion 20.

As in the prior examples, all dimensions of all components of the specimen positioning system 10 are registered, coordinated and matched with those on the respective imaging systems. In this case, they are registered with the drive table 152 and bore 158 so that the imaging area 106 will nominally be positioned within the sweet spot or centerline of the field of view within bore 158 upon controlled and coordinated actuation of drive table 152.

It can now be appreciated that the present invention provides a working system which coordinates all specimen and accompanying coil placements within the field of view of each imaging system for proper referencing. This minimizes the guesswork of where a gradient coil is positioned, where an RF probe is positioned and where/how the animal or specimen is located in relation to the centerline of the field of view of the imaging system, as all components as well as the specimen are referenced from the same relative zero point. It becomes as simple as placing the animal onto the animal holder, interfacing and connecting the animal holder with a machine specific positioning receiver assembly 14, and in the case of an MRI type imaging machine, interfacing the V-grooves and rails of the positioning assembly system 90, and sliding the animal management system 10 into the magnet bore until a mechanical stop engages a reference surface. At this point, the specimen is properly located to be imaged.

When the animal management system 10 is not utilized in an MRI type system, all these attributes are still maintained via the positioning receiver assembly 14. An operator simply loads an animal into a predetermined fixed position within the animal holder 12, and then engages the animal holder 12 with the imaging machine via a specific positioning receiver assembly 14 mounted to the imaging machine.

These characteristics of the invention form the mechanical basis that properly positions the animal within the field of view of each imaging machine. If an operator is running a series of images on different machines (modalities) with the same animal, once the animal is placed onto the animal holder 12, it is passed between and interfaced with the different machines via the machine specific positioning receivers 14, which allow for the connection of the animal holder to the machine.

For example, a research protocol could begin with an MRI scan. When the MRI scan is done, the animal management system 10 is then removed from the bore of the MRI magnet. The animal holder 12 is then disengaged from the positioning receiver assembly 14 and moved to the next imaging modality and placed in the positioning receiver assembly 14 on the next imaging machine, such as a micro CT machine. Since each imaging machine has a machine specific positioning receiver assembly already on it, the researcher merely engages the coupling 16, locks the animal holder into place via the locking lever 28, and starts the next scanning session with the specimen automatically properly positioned for optimum imaging results.

There has been disclosed heretofore the best embodiment of the invention presently contemplated. Obviously, numerous modifications and variations of the present invention are possible in light of the above teachings. It is therefore to be understood that within the scope of the appended claims, the invention may be practiced otherwise than as specifically described herein.

What is claimed is:

1. A positioning system for an imaging machine, comprising:
    an animal holding assembly comprising a specimen alignment bed having a support surface configured to contact and hold an animal in a predetermined position on said support surface;
    a positioning receiver assembly connecting said animal holding assembly to an imaging machine;
    a releasable coupling having a first coupling portion coupled to said imaging machine and a second coupling portion coupled to said specimen alignment bed on said animal holding assembly, said releasable coupling releasably interconnecting said animal holding assembly and said positioning receiver assembly in a repeatable predetermined coupled position to facilitate registration and alignment of said specimen alignment bed and said animal in the imaging machine; and
    wherein said coupling comprises an interconnection panel having internal ports for communicating with wires and tubes.

2. The system of claim 1, further comprising a keying alignment feature provided within said coupling and comprising a male keying member guided into a female keying member and aligning said first and second coupling portions.

3. The system of claim 1, wherein said animal holding assembly comprises a hermetically sealed closed animal holding chamber.

4. The system of claim 1, further comprising a head holder selected from the group consisting of a bite bar, ear bars, and a head clamp.

5. The system of claim 1, further comprising an elongated closed tube internally receiving said specimen alignment bed and coupled to said animal holding assembly.

6. A method of imaging a specimen in a first imaging machine having an axial bore and a first receiver with a first receiver coupling portion for enabling production of accurate, repeatable images of the specimen taken over a period of time, said method comprising:
    mounting a specimen in a holder, said holder having a first holder coupling portion;
    providing an axially releasable coupling between said holder and said first receiver, said axially releasable coupling comprising said first holder coupling portion and said first receiver coupling portion aligned along an axis;
    mounting said holder on said first receiver in a predetermined axial position by axially engaging said first holder coupling portion with said first receiver coupling portion so that the specimen is positioned in a predetermined axial position on said first receiver;
    channeling a fluid through a closed flowpath through said first holder coupling portion and through said first receiver coupling portion and adjacent to the specimen;
    positioning said holder within a field of view of said first imaging machine, using said first receiver such that the axis of the releasable coupling extends axially within the axial bore;
    taking an image of said specimen with said first imaging machine;
    removing said holder from said field of view; and
    removing said holder from said first receiver by axially releasing said coupling.

7. A positioning system for an imaging machine having an axis, comprising:
    an animal holding assembly comprising a specimen alignment bed having a support surface configured to contact and hold an animal in a predetermined position on said support surface;
    a positioning receiver assembly coupling said animal holding assembly to an imaging machine;
    a releasable coupling having a first coupling portion coupled to said imaging machine and a second coupling portion coupled to said specimen alignment bed on said animal holding assembly, said releasable coupling releasably interconnecting said animal holding assembly and said positioning receiver assembly in a repeatable predetermined coupled position to facilitate registration and alignment of said specimen alignment bed and said animal in the imaging machine; and
    a keying alignment feature provided on said coupling and comprising a male keying member guided into a female keying portion and aligning said first and second coupling portions.

8. A positioning system for an imaging machine, comprising:
- an animal holding assembly comprising a specimen alignment bed having a support surface configured to contact and hold an animal in a predetermined position on said support surface;
- a positioning receiver assembly connecting said animal holding assembly to an imaging machine;
- a releasable coupling having a first coupling portion coupled to said imaging machine and a second coupling portion coupled to said specimen alignment bed on said animal holding assembly, said releasable coupling releasably interconnecting said animal holding assembly and said positioning receiver assembly in a repeatable predetermined coupled position to facilitate registration and alignment of said specimen alignment bed and said animal in the imaging machine; and
- an elongated closed tube internally receiving said specimen alignment bed and coupled to said animal holding assembly with a sliding hermetically sealed interconnection.

9. A positioning system for an imaging machine having an axial bore, comprising:
- an animal holding assembly comprising a specimen alignment bed having a support surface configured to contact and hold an animal in a predetermined position on said support surface;
- a positioning receiver assembly connecting said animal holding assembly to an imaging machine; and
- an axially releasable coaxial coupling having an axis and having a first coupling portion coupled to said imaging machine and a second coupling portion coupled to said specimen alignment bed on said animal holding assembly, said releasable coupling releasably interconnecting said animal holding assembly and said positioning receiver assembly in a repeatable predetermined coaxially coupled position with the axis of the releasable coupling extending axially within the axial bore of the imaging machine to facilitate registration and alignment of said specimen alignment bed and said animal in the imaging machine.

* * * * *